United States Patent
Brown et al.

(10) Patent No.: US 9,247,159 B2
(45) Date of Patent: Jan. 26, 2016

(54) INFRARED CAMERA DETECTION SYSTEMS AND METHODS

(71) Applicant: FLIR Systems, Inc., Wilsonville, OR (US)

(72) Inventors: Andrew Phillip Brown, Goleta, CA (US); Nicholas Högasten, Santa Barbara, CA (US); Austin A. Richards, Santa Barbara, CA (US)

(73) Assignee: FLIR Systems, Inc., Wilsonville, OR (US)

(*) Notice: Subject to any disclaimer, the term of this patent is extended or adjusted under 35 U.S.C. 154(b) by 337 days.

(21) Appl. No.: 13/762,255

(22) Filed: Feb. 7, 2013

(65) Prior Publication Data
US 2013/0147951 A1 Jun. 13, 2013

Related U.S. Application Data

(63) Continuation of application No. PCT/US2011/047489, filed on Aug. 11, 2011.

(60) Provisional application No. 61/372,644, filed on Aug. 11, 2010.

(51) Int. Cl.
*G06K 9/00* (2006.01)
*H04N 5/33* (2006.01)
(Continued)

(52) U.S. Cl.
CPC ............... *H04N 5/33* (2013.01); *G01N 25/18* (2013.01); *G01N 33/1833* (2013.01); *G06K 9/00523* (2013.01); *G06T 7/0004* (2013.01);
(Continued)

(58) Field of Classification Search
CPC ............ G01N 25/18; G01N 33/1833; G01N 33/1826; G01N 33/18; G06K 9/00523; G06T 2207/10048; G06T 2207/20076; G06T 2207/30108; G06T 2207/30181; G06T 7/0004; G06T 7/0008; G06T 7/0081; G06T 2207/10016; G06T 2207/10032; G06T 7/00; G06T 7/20; H04N 5/33
USPC .......................................................... 348/143
See application file for complete search history.

(56) References Cited

U.S. PATENT DOCUMENTS 3,719,936 A * 3/1973 Daniels et al. ..................... 441/1
5,532,679 A * 7/1996 Baxter, Jr. ................. 340/539.26
(Continued)

FOREIGN PATENT DOCUMENTS

WO   WO 2009/023552   2/2009

OTHER PUBLICATIONS

Grimaldi C.S.L et al, Near Real Time Oil Spill Detection and Monitoring Using Satellite Optical Data, 2009.*
(Continued)

*Primary Examiner* — Shan Elahi
(74) *Attorney, Agent, or Firm* — Haynes and Boone, LLP

(57) ABSTRACT

Infrared imaging systems and methods disclosed herein, in accordance with one or more embodiments, provide for detecting petroleum in an infrared image. The detection involves the evaluation of local background model likelihoods in light of extracted pixel features as well as the evaluation of a global outlier model in light of extracted pixel features. Those pixels having a low likelihood for both their local background model as well as the outlier model are identified as corresponding to oil-contaminated water within the infrared image.

20 Claims, 6 Drawing Sheets

(51) Int. Cl.
  *G01N 25/18*   (2006.01)
  *G01N 33/18*   (2006.01)
  *G06T 7/00*   (2006.01)

(52) U.S. Cl.
  CPC ............... *G06T2207/10048* (2013.01); *G06T 2207/20076* (2013.01); *G06T 2207/30108* (2013.01); *G06T 2207/30181* (2013.01)

(56) References Cited

U.S. PATENT DOCUMENTS

| | | | |
|---|---|---|---|
| 7,728,291 B2 * | 6/2010 | Bello | 250/301 |
| 8,124,931 B2 * | 2/2012 | Andrews et al. | 250/301 |
| 8,362,429 B2 * | 1/2013 | Andrews et al. | 250/339.14 |
| 2005/0027188 A1 * | 2/2005 | Metaxas et al. | 600/410 |
| 2005/0122225 A1 * | 6/2005 | Kram et al. | 340/605 |
| 2008/0239091 A1 * | 10/2008 | Soga | 348/222.1 |
| 2009/0039255 A1 * | 2/2009 | Andrews et al. | 250/301 |
| 2009/0067716 A1 * | 3/2009 | Brown et al. | 382/173 |
| 2010/0309315 A1 * | 12/2010 | Hogasten et al. | 348/164 |

OTHER PUBLICATIONS

Casciello et al, Robust Satellite Techiques (RST) for Oil Spill Detection and Monitoring, 2007.*

Madar et al., "Local-Global Background Modeling for Anomaly Detection in Hyperspectral Images", Hyperspectral Image and Signal Processing, Evolution in Remote Sensing, 2009, Whispers '09. First Workshop on, IEEE, Aug. 26, 2009, pp. 1-4, Piscataway, New Jersey, USA.

Tang et al., "A New Outlier Detection Algorithm Based on Manifold Learning", Control and Decision Conference (CCDC), 2010 Chinese, IEEE, May 26, 2010, pp. 452-457, Piscataway, New Jersey, USA.

Xu, et al., "Small Target Detection Based on Maximum Background Model in IR Images", Acta Photonica Sinica, Dec. 2002, pp. 1483-1486. vol. 31, No. 12, China.

* cited by examiner

INFRARED CAMERA DETECTION SYSTEMS AND METHODS

CROSS-REFERENCE TO RELATED APPLICATIONS

This continuation patent application claims priority to and the benefit of PCT Patent Application No. PCT/US2011/047489 filed Aug. 11, 2011, which claims priority to and the benefit of U.S. Provisional Patent Application No. 61/372,644 filed Aug. 11, 2010, both of which are incorporated herein by reference in their entirety.

TECHNICAL FIELD

The present disclosure relates to infrared imaging systems and, in particular, to infrared camera detection systems and methods.

BACKGROUND

A petroleum spill in water presents a special challenge for imaging systems based on visible detection methods. For example, ocean water is often turbid and appears dark to the eye, as does crude oil. Crude oil or diesel spills may float to the surface because of their lower density and may form well-defined films, especially in still waters. However, oil films may not show a strong contrast relative to the water surface itself, at least to the unaided eye. This may occur in water that is choppy or covered in waves, because the water surface may alternately look dark or light depending on how the water reflects the sky or the sun above it, thus masking low contrast oil-film areas. Accordingly, there exists a need for an improved imaging system that may be used for oil spill detection applications.

SUMMARY

Infrared imaging systems and methods disclosed herein, in accordance with one or more embodiments, provide for infrared camera detection techniques including detecting petroleum (e.g., oil, diesel, or other petrochemicals) in an infrared image. The petroleum, as an example, may be within a body of water, such as on a surface of a body of water. The petroleum, for example, may cluster (i.e., gather or form together in a film, tar ball, or glob) and cover a portion of the body of water being imaged.

Each frame of an infrared image is composed of many digital pixels. These digital pixels may each be characterized individually or represented by a downsampled version. With the water surface unpolluted by water or other obstructions, a sensor having a fixed field of view of the water surface will provide sequential frames of infrared images of the same water surface area. Each pixel can be examined to extract features such as intensity, contrast, and energy within a certain bandwidth. Regardless of the type of feature extracted from each of the pixels, these features will have a certain statistical behavior that can be predicted over time. The statistical behavior of the extracted features is denoted herein as a local background model.

The local background model is based upon "normal" water behavior that is unpolluted by oil or other obstructions. Thus, whereas the local background model (LBM) can be expected to be considered as highly likely for any given normal pixel's features, the same local background model can be expected to be highly unlikely with regard to a feature observation for a pixel from an image of oil-contaminated water surface. In one embodiment, the local background model is constructed using a mixture of Gaussians model (MGM). As infrared images are collected, each pixel (or downsampled version thereof) may be tested against its LBM to determine the likelihood of the LBM. Since the LBM will change as sea surfaces change, the LBM is continually updated as image frames are produced. This updating is damped so that a short sequence of anomalous events does not skew the local model.

There are, however, non-oil-related outlier events that will produce pixel features that make the LBM unlikely. For example, obstructions such as kelp or other floating objects, glint, and fixed structures will produce pixel features that make the LBM unlikely despite there being no oil contamination. To prevent false alarms from such outliers, a global outlier model (OM) for extracted features is developed. Just like the LBM, the OM is a statistical model for extracted feature likelihood. An observed feature for a given pixel can thus be evaluated under the OM to determine whether the OM is likely or unlikely. Since the OM is to model outliers rather than normal water behavior, it is not updated equally on each new frame as occurs for the LBM. Instead, the OM is skewed towards anomalous events by weighting the pixels according to their probability under the LBM. To lower computation complexity, this updating may occur for some least-likely fraction of the pixels as evaluated under the LBM.

The scope of the disclosure is defined by the claims, which are incorporated into this section by reference. A more complete understanding of embodiments of the present disclosure will be afforded to those skilled in the art, as well as a realization of additional advantages thereof, by a consideration of the following detailed description of one or more embodiments. Reference will be made to the appended sheets of drawings that will first be described briefly.

BRIEF DESCRIPTION OF THE DRAWINGS

Embodiments of the present disclosure and their advantages are best understood by referring to the detailed description that follows. It should be appreciated that like reference numerals are used to identify like elements illustrated in one or more of the figures.

DETAILED DESCRIPTION

Figure 1:
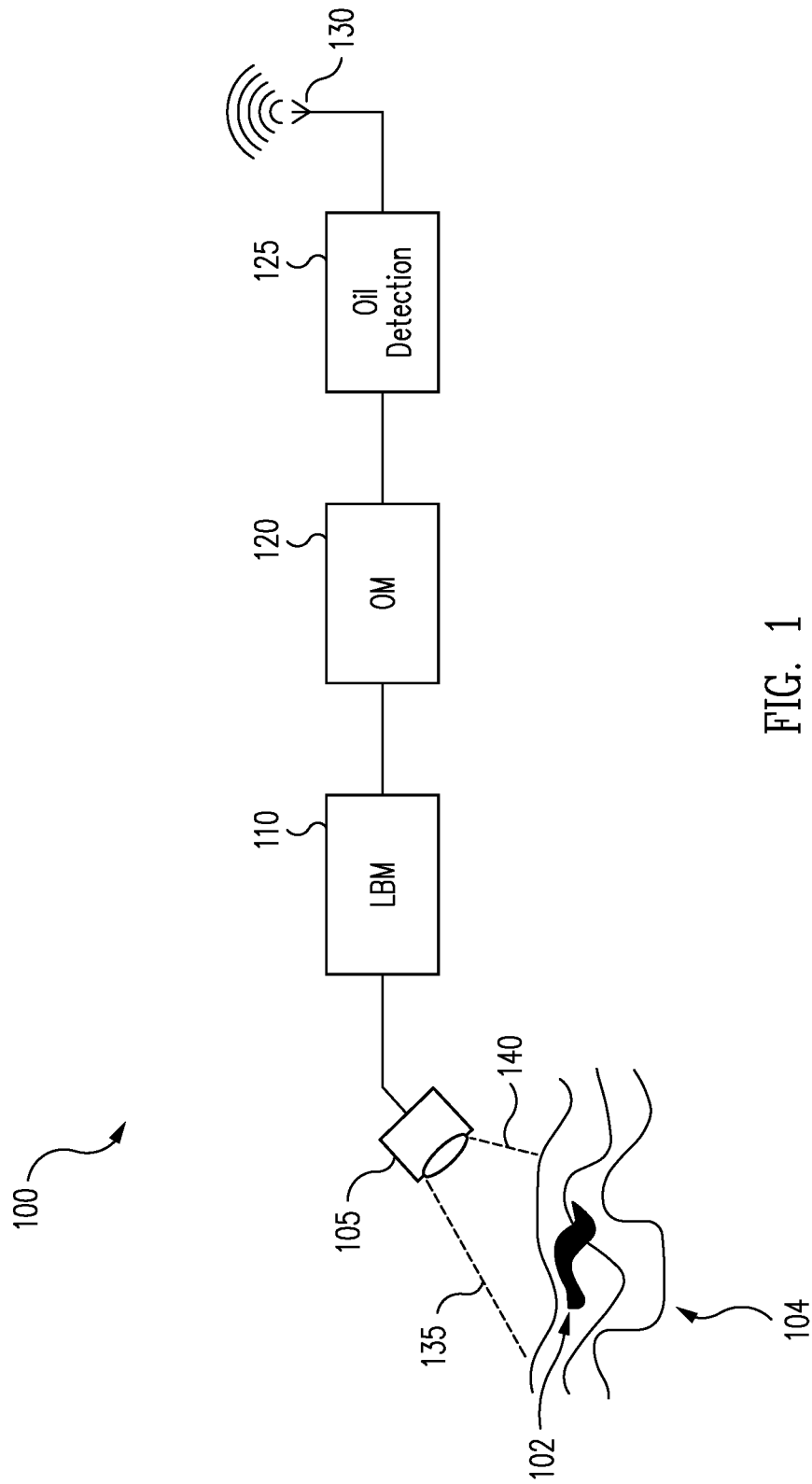
FIG. 1 shows an overview of a process for detecting a petroleum cluster on water in infrared images, in accordance with an embodiment.

Petroleum spills in water present a special challenge for imaging systems based on conventional visible detection methods. For example, ocean water is often turbid and appears dark to the eye, as does crude oil. In another example, crude oil or diesel spills may float to the surface because of their lower density and may form well-defined films especially in still waters. However, oil films may not show a strong contrast to the water surface itself, at least to the unaided eye. This may occur in water that is choppy or covered in waves, because the water surface may alternately look dark or light depending on how the water reflects the sky or the sun above it, thus masking low contrast oil-film areas. Accordingly, thermal infrared imaging as disclosed herein is a viable alternative for spill detection and is effective for a number of reasons.

For example, the lighting of an ocean surface scene is highly variable in the visible band, but is typically very uniform in the thermal infrared band. Visible light levels may vary by as much as a factor of 100 million between a bright sunny day and an overcast night with no moon or artificial light sources, while thermal IR light levels may only change by a factor of two at most. Thermal infrared (IR) scenes are always intrinsically lit by IR emission from the scene itself, but visible-light imaging systems may require a source of light at night, which is an inconvenience for imaging-based detection systems that use visible light as a means to identify oil spills.

Furthermore, the surfaces of natural bodies of water are often very non-uniform reflectors in the visible band, especially when there are waves, chop, or windy conditions. Surface waves may act like alternating convex and concave mirrors, thus changing the apparent brightness of the water surface rapidly and easily hiding surface features, such as floating oil. In addition, solar interference may be a huge problem for visible-light systems, wherein a camera may be blinded from sunlight reflecting off the water surface, especially at sunrise or sunset, if the camera is looking towards the sun. In contrast, thermal IR cameras are much less sensitive to the sun, since the sun peaks in the visible part of the electromagnetic (EM) spectrum, around 500 nm in wavelength. Even on a cloudy day, where the visible light illumination is much more uniform, the degree of variability of the water surface brightness may change rapidly due to the reflectivity effects of surface conditions. This is quite different from thermal TR light, which is both a smaller component of sunlight and which is emitted by the water surface itself. This brightness uniformity found in the thermal IR bands sets the stage for practical detection of oil spills.

Additionally for infrared, oil or diesel film on the surface of water tends to look quite different from the water itself, giving floating films of oil a very distinct appearance. Oil tends to look darker than water in the long wave IR band, for example, while oil tends to look lighter than water in the mid wave IR band. The reasons for this are a complex mix of phenomena, involving the reflective and refractive index properties of water and oil, interference effects seen in thin films, and the emissivity of oil and water in both the near and thermal IR wavebands. For example, a thick film of oil may be more reflective than water because of a higher bulk index of refraction. It may therefore emit less IR light than the water even if it is at the same temperature as the water, as well as reflecting the cold sky above it into the camera lens. This means that thick oil films may tend to look darker than the water, depending on other competing optical effects, such as sunlight heating the film and cooling due to wind.

Signal processing algorithms are disclosed herein that advantageously exploit these advantageous properties of long wave infrared (LWIR) imagery to detect petroleum spills on water. Although these algorithms are described with regard to the detection of oil, the algorithms may be more generally applied to the detection of other water surface anomalies such as semi-submerged shipping containers or other shipping hazards. Turning now to the drawings, FIG. 1 shows an overview 100 of the signal processing algorithms.

An uncooled, long wave infrared (LWIR) sensor 105 such as a microbolometer is positioned to have a fixed field of view with regard to a water surface 104. Because sensor 105 has a fixed field of view, there is no motion that would change the field of view. In this fashion, the rather complex and challenging background behavior for water surface 104 may be learned without the added complication of a changing field of view. However, it will be appreciated that the signal processing algorithms disclosed herein may be extended in a straightforward manner to a moving sensor application by registering the background models developed by the algorithms to align with the current sensor field of view Automated detection of a petroleum-containing contaminant such as an oil spill 102 is a formidable problem. Sea states can change drastically from glassy conditions to whitecaps. In addition to the sea state, the lighting conditions can also change dramatically from bright and sunny to dark and overcast. The resulting infrared image of water surface 104, even with the simplification of a fixed field of view, thus changes dramatically over time. Moreover, the contrast of oil itself can change as it drifts and bobs in the waves. In one instance, the oil may have a greater intensity than the surrounding water whereas in a next instance the oil may have a smaller intensity than the surrounding water. To meet such a challenging detection problem, an image stream from sensor 105 is processed to develop a local background model (LBM) 110 as well as an outlier model (OM) 120.

LBM 110 provides statistical modeling for individual pixels with regard to extracted image features. To model the local background, LBM 110 is developed over some arbitrary number of image frames—for example, 300 frames may be analyzed to develop LBM 110. In one embodiment, LBM 110 is learned continually over all time (except when or where oil is detected in the field of view) via temporal damping with a large time constant. Each image pixel may have its own local background model. Alternatively, the original image pixels may be downsampled such that only downsampled pixels have an individual local background model. Downsampling reduces the number of pixels being modeled and thus reduces computational complexity. However, since the algorithms disclosed herein are independent of whether downsampling is implemented or not, the term "pixel" is used herein to generically refer to image pixels, regardless of whether that "pixel" is actually a downsampled version of original image pixels or whether that "pixel" is actually an original image pixel. As discussed above, the infrared image of water surface 104 will change as the sea states and lighting conditions change. Other variables that will affect the sensed image over time include the ambient air temperature as well as the water temperature. To keep LBM 110 up to date as the local conditions change, it is continually updated based upon current frame image data. In this fashion, LBM 110 reflects the local "normal" behavior. Assuming that LBM 110 is created over clear water, it will thus detect changes resulting from anomalies such as oil. However, there are many sorts of anomalies besides oil that would produce an image having features that lie outside of the expected behavior established by LBM 110. For example, kelp or other types of seaweed may be floating on the water surface. Alternatively, objects and detritus may be floating as well. Moreover, the fixed field of view may include portions of the oil platform or buoys that will certainly produce image features that lie outside of the norm established by unobstructed water surface. Thus, an algorithm that merely alarmed whenever LBM 110 indicates there is a group of adjacent pixels with anomalous image features would produce an undesirable amount of false oil detections.

OM 120 prevents or minimizes such false alarms by modeling anomalies besides oil. In that regard, OM 120 models the behavior of outlier pixels. In other words, LBM 110 is used to identify pixels having image features that are deemed anomalous as compared to the expected behavior of water surface 104. There are many LBMs since there in LBM 110 for each modeled pixel In contrast, there is only one OM 120, which models the statistical properties of relatively rare events for all the pixels. OM 120 thus provides a statistical model for extracted features corresponding to these relatively rare events. However, the extracted features used to build OM 120 may be independent from those used in LBM 110. For example, a pixel at a far end 135 of the field of view may represent a relatively large range variation whereas pixel at on opposing near end 140 of the field of view may represent a relatively small range variation. Thus, a pixel corresponding to far end 135 will represent a significantly larger amount of water surface area as opposed to a pixel from near end 140. To keep the false alarm rate constant regardless of range, OM 120 should be dependent upon range. Thus, one of the extracted features used to develop OM 110 should be range.

Just like LBM 110, OM 120 is updated continuously as new image data is processed. However, LBM 110 is updated from every frame in that it is modeling normal behavior. Since the vast majority of frames represent normal (no oil) events, LBM 110 needs to be updated based upon all the frames. If oil is detected, however, updating of LBM 110 is ceased until normal conditions return. But while LBM 110 is updating, each frame is given equal weight since LBM 110 is individual to each pixel. In contrast, OM 120 represents the statistical behavior of relatively rare extracted feature values for all pixels Thus, OM 120 should not be updated equally by all pixels but instead only by those pixels having statistically anomalous values as identified by LBM 110. For example, OM 120 can be updated by weighting each pixel. Alternatively, just a fraction of the total pixels in any given frame are identified as being worthy of weights—for example, the pixels having the top 40% least likely scores from their LBMs may be used to update OM 120. Regardless of whether all pixels are used in this fashion or just a fraction of the pixels are used, the resulting pixels may be weighted according to their probability under their LBM and also normalized to compensate for the non-uniform distribution of feature values. OM 120 may then be updated based upon the resulting weighted and normalized pixels as discussed further herein. The end result is that pixels generating small likelihoods for their LBM 110 will be assigned large weights in updating OM 120.

An oil detection algorithm 125 thus determines whether a group of adjacent pixels are anomalous with regard to both LBM 110 and OM 120, since such pixels may be safely assumed to represent oil in that other sorts of outlier causes would not be deemed as anomalous by OM 120. The resulting oil detection may be transmitted to an operator using a wireless connection 130. Alternatively, the transmission may occur through a wired link. In this fashion, sensor 105 may be installed on an unmanned rig yet personnel can be notified in virtual real-time of any oil leaks or spills This is quite beneficial as the standard practice is that such oil rigs must be inspected weekly by boat crews to investigate the presence of oil leaks. This is not only expensive but also enables leaks to occur for days until the inspection crew arrives. In contrast, LBM 110 and OM 120 enable a real-time yet inexpensive way to automatically detect such oil spills. Moreover, if a crew were to arrive in response to an alarm over link 130 yet find no oil, the anomaly that lead to such a false alarm may be used to revise OM 120. In this fashion, OM 120 becomes ever more adept at identifying non-oil-caused anomalies.

Figure 2:
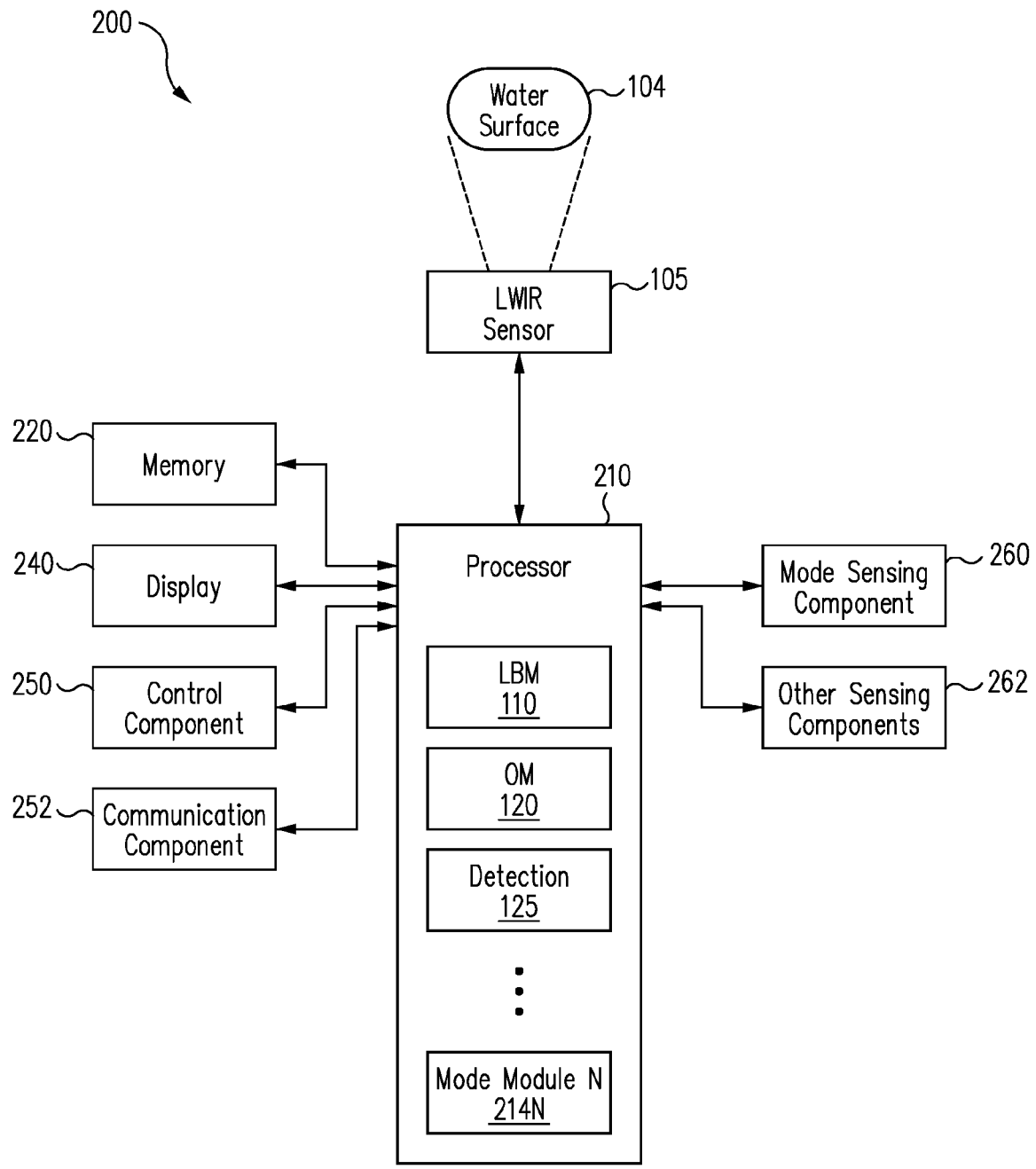
FIG. 2 shows a block diagram illustrating an infrared imaging system for capturing and processing infrared images, including detecting petroleum in an infrared image, in accordance with one or more embodiments.

LBM 110, OM 120, and oil detection algorithm 125 may all be implemented using a suitably programmed logic engine or processor such as a programmed microprocessor or microcontroller, a configured field programmable gate array (FPGA), or an ASIC. FIG. 2 shows a block diagram illustrating an infrared imaging system 200 for capturing and processing infrared images, including detecting petroleum in an infrared image. A processor 210 implements LBM 110 and OM 120 as well as detection algorithm 125.

In various embodiments, infrared imaging system 200 may include one or more of a memory 220, a display 240, a control component 250, and/or a mode sensing component 260. In one embodiment, infrared imaging system 200 may include one or more of a communication component 252 and one or more other sensing components 262 or other elements of infrared imaging system 200, depending upon the requirements and application.

Processor 210 may be implemented with a microprocessor, such as a single-core microprocessor, a multi-core microprocessor. Alternatively, processor 210 may comprise a microcontroller, a logic device (e.g., a programmable logic device configured to perform processing functions), a digital signal processing (DSP) device, or some other type of generally known processor. Processor 210 is adapted to interface and communicate with elements 220, 240, 250, 252, 260, and 262 to perform method and processing steps as described herein.

In various embodiments, processor 210 may include one or more mode modules 214A-214N for operating in one or more modes of operation. FIG. 2 shows only module 214N for illustration clarity. In one aspect, mode modules 214A-214N are adapted to define preset processing and/or, display functions that may be embedded in processor 210 or stored on memory 220 for access and execution by processor 210. In another aspect, processor 210 may be adapted to perform various types of image processing algorithms to enhance the infrared images.

In various embodiments, it should be appreciated that LBM 110, OM 120 and/or each mode module 214A-214N may be integrated in software and/or hardware as part of processor 210, or as code stored in memory 220. Embodiments of LBM 110, OM 120 and/or each mode module 214A-214N (i.e., modes of operation) disclosed herein may be stored by a separate computer-readable medium (e.g., a memory, such as a hard drive, a compact disk, a digital video disk, or a flash memory) to be executed by a computer (e.g., logic or processor-based system) to perform various methods disclosed herein.

In one example, the computer-readable medium may be portable and/or located separate from infrared imaging system 200, with LBM 110, OM 120 and/or each mode module 214A-214N provided to infrared imaging system 200 by coupling the computer-readable medium to infrared imaging system 200 and/or by infrared imaging system 200 downloading (e.g., via a wired or wireless link) LBM 110, OM 120 and/or each mode module 214A-214N from the computer-readable medium (e.g., containing the non-transitory information).

Memory 220 includes, in one embodiment, one or more memory devices to store data and information. The one or more memory devices may include various types of memory including volatile and non-volatile memory devices, such as RAM (Random Access Memory), ROM (Read-Only Memory), EEPROM (Electrically-Erasable Read-Only Memory), flash memory, etc. In one embodiment, processor 210 is adapted to execute software stored in memory 220 to perform various methods, processes, and modes of operations in manner as described herein.

Image sensor 105 includes, in one embodiment, one or more infrared sensors (e.g., any type of infrared detector, such as a focal plane array) for capturing infrared image signals representative of an image, such as an image of water surface 104. Sensor 105 represents a captured image signal of water surface 104 as digital data (e.g., via an analog-to-digital converter included as part of the infrared sensor or separate from the infrared sensor as part of infrared imaging system 200). Processor 210 is adapted to receive infrared image signals from sensor 105, to process the infrared image signals (e.g., to provide processed image data), to store infrared image signals or image data in memory 220, and/or retrieve stored infrared image signals from memory 220. Processor 210 may be adapted to process infrared image signals stored in memory 220 to provide image data (e.g., captured and/or processed infrared image data) to display component 240 for viewing by a user.

Display component 240 includes, in one embodiment, an image display device (e.g., a liquid crystal display (LCD)) or various other types of generally known video displays or monitors. Processor 210 may be adapted to display image data and information on display 240. Processor 210 may be adapted to retrieve image data and information from memory 220 and display any retrieved image data and information on display 240. Display component 240 may include display electronics, which may be utilized by processing component 110 to display image data and information (e.g., infrared images). Display component 240 may receive image data and information directly from sensor 105 via processor 210, or the image data and information may be transferred from memory 220 via processor 210.

Control component 250 includes, in one embodiment, a user input and/or interface device having one or more user actuated components. For example, the actuated components may include one or more push buttons, slide bars, rotatable knobs, and/or a keyboard, which are adapted to generate one or more user actuated input control signals. Control component 250 may be adapted to be integrated as part of display 240 to function as both a user input device and a display device, such as, for example, a touch screen device adapted to receive input signals from a user touching different parts of the display screen. Processor 210 may be adapted to sense control input signals from control component 250 and respond to any sensed control input signals received therefrom.

Control component 250 may include, in one embodiment, a control panel unit (e.g., a wired or wireless handheld control unit) having one or more user-activated mechanisms (e.g., buttons, knobs, sliders, etc.) adapted to interface with a user and receive user input control signals. In various embodiments, the one or more user-activated mechanisms of the control panel unit may be utilized to select various modes of operation in reference to mode modules 214A-214N.

As such, it should be appreciated that the control panel unit may be adapted to include one or more other user-activated mechanisms to provide various other control functions of infrared imaging system 200, such as auto-focus, menu enable and selection, field of view (FoV), brightness, contrast, gain, offset, spatial, temporal, and/or various other features and/or parameters. In still other embodiments, a variable gain signal may be adjusted by the user or operator based on a selected mode of operation. In another embodiment, control component 250 may include a graphical user interface (GUI), which may be integrated as part of display 240 (e.g., a user actuated touch screen), having one or more images of the user-activated mechanisms (e.g., buttons, knobs, sliders, etc.), which are adapted to interface with a user and receive user input control signals via the display 240.

Infrared imaging system 200, in accordance with one or more embodiments, may serve as a sensor adapted to automatically detect a petroleum spill. For example, sensor 105 may represent an uncooled, long wave infrared (LWIR), microbolometer sensor. In one exemplary application, using the emissivity difference between seawater and petroleum in the LWIR band, a microbolometer detector may be used to find petroleum spills. Thus, an inexpensive, compact, single waveband sensor may be used to detect a petroleum spill using the techniques disclosed herein. For example for an embodiment, by processor 210 applying LBM 110, OM 120 and detection algorithm 125 to the infrared images, petroleum may be classified in the infrared images (e.g., snapshots and/or video) and separated from waves, reflections, etc., as described herein.

In one embodiment, the infrared imaging system 200 may be adapted for automatic detection, including petroleum spills not visible to the human eye, such as diesel fuel spills. As such, unmanned oil rigs may be automatically checked for leaks without human intervention, and petroleum leaks may be detected early. The infrared imaging system 200 may be adapted to operate at night with no illumination.

Mode sensing component 260 includes, in one embodiment, an application sensor adapted to automatically sense a mode of operation, depending on the sensed application (e.g., intended use or implementation), and provide related information to processor 210. In various embodiments, the application sensor may include a mechanical triggering mechanism (e.g., a clamp, clip, hook, switch, push-button, etc.), an electronic triggering mechanism (e.g., an electronic switch, push-button, electrical signal, electrical connection, etc.), an electro-mechanical triggering mechanism, an electro-magnetic triggering mechanism, or some combination thereof. Alternatively, the mode of operation may be provided via control component 250 by a user of infrared imaging system 200. Processor 210 may be adapted to communicate with mode sensing component 260 (e.g., by receiving sensor information from mode sensing component 260) and sensor 105 (e.g., by receiving data and information from sensor 105 and providing and/or receiving command, control, and/or other information to and/or from other components of infrared imaging system 100).

In various embodiments, mode sensing component 260 may be adapted to provide data and information relating to system application including a handheld implementation and/or coupling implementation associated with various types of vehicles (e.g., a land-based vehicle, a watercraft, an oil rig, an aircraft, a spacecraft, etc.). In one embodiment, mode sensing component 260 may include communication devices that relay information to processor 210 via wireless communication. For example, mode sensing component 260 may be adapted to receive and/or provide information through a satellite, through a local broadcast transmission (e.g., radio frequency), through a mobile or cellular network and/or through information beacons in an infrastructure (e.g., a transportation or highway information beacon infrastructure) or various other wired or wireless techniques.

In another embodiment, infrared imaging system 200 may include one or more other types of sensing components 262, including environmental and/or operational sensors, depending on the sensed application or implementation, which provide information to processor 210 (e.g., by receiving sensor information from each sensing component 262). In various embodiments, other sensing components 262 may be adapted to provide data and information related to environmental conditions, such as internal and/or external temperature conditions, lighting conditions (e.g., day, night, dusk, and/or dawn), humidity levels, specific weather conditions (e.g., sun, rain, and/or snow), distance (e.g., laser rangefinder), and/or whether a tunnel, a covered parking garage, or that some type of enclosure has been entered or exited. Accordingly, other sensing components 262 may include one or more conventional sensors as would be known by those skilled in the art for monitoring various conditions (e.g., environmental conditions) that may have an effect (e.g., on the image appearance) on the data provided by sensor 105.

In some embodiments, other sensing components 262 may include devices that relay information to processor 210 via wireless communication. For example, each sensing component 262 may be adapted to receive information from a satellite, through a local broadcast (e.g., radio frequency) transmission, through a mobile or cellular network and/or through information beacons in an infrastructure (e.g., a transportation or highway information beacon infrastructure) or various other wired or wireless techniques.

In various embodiments, components of infrared imaging system 200 may be combined and/or implemented or not, as desired or depending on application requirements, with infrared imaging system 200 representing various functional blocks of a system. For example, processor 210 may be combined with memory 220, sensor 105, display 240, and/or mode sensing component 260. As a further example, infrared imaging system 200 may represent a networked system, with sensor 105 being remote from certain other portions of infrared imaging system 200. In still another example, control component 250 may be combined with one or more other components or be remotely connected to at least one other component, such as processor 210, via a wired or wireless control device so as to provide control signals thereto.

In one embodiment, communication component 252 may comprise a network interface component (NIC) adapted for communication with a network including other devices. In various embodiments, communication component 252 may include a wireless communication component, such as a wireless local area network (WLAN) component based on the IEEE 802.11 standards, a wireless broadband component, mobile cellular component, a wireless satellite component, or various other types of wireless communication components adapted for communication with a network. As such, communication component 252 may include an antenna coupled thereto for wireless communication purposes. In other embodiments, the communication component 252 may be adapted to interface with a DSL (e.g., Digital Subscriber Line) modem, a PSTN (Public Switched Telephone Network) modem, an Ethernet device, and/or various other types of wired and/or wireless network communication devices adapted for communication with a network.

In various embodiments, a network may be implemented as a single network or a combination of multiple networks. For example, in various embodiments, the network may include the Internet and/or one or more intranets, landline networks, wireless networks, and/or other appropriate types of communication networks. In another example, the network may include a wireless telecommunications network (e.g., cellular phone network) adapted to communicate with other communication networks, such as the Internet. As such, in various embodiments, the infrared imaging system 100 may be associated with a particular network link such as for example a URL (Uniform Resource Locator), an IP (Internet Protocol) address, and/or a mobile phone number.

Figure 3:
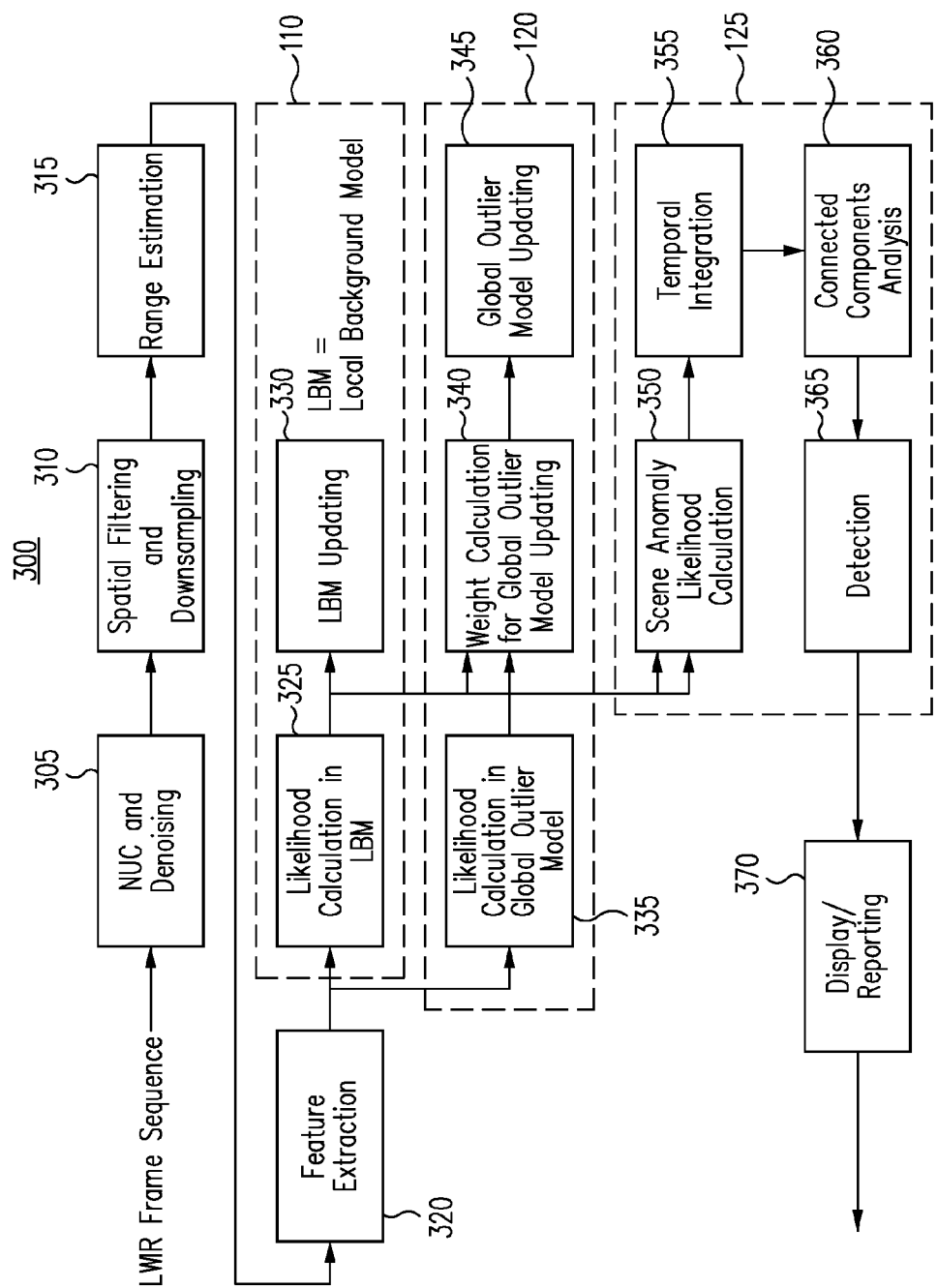
FIG. 3 shows an overview of a process for detecting a petroleum cluster in infrared images, in accordance with an embodiment.

Having thus provided an overview of the signal processing algorithms as well as a system for implementing those algorithms, the algorithms will now be discussed in more detail. FIG. 3 is a block diagram of the algorithmic process 300. A LWIR frame sequence is initially processed using a nonuniformity correction (NUC) and denoising algorithm 305 as known in the image processing arts. To reduce computational load on processor 210 as well as to increase the image signal-to-noise ratio, the output frames from algorithm 305 are processed by a spatial filtering and downsampling algorithm 310 such that neighboring pixels are averaged to produce downsampled pixels. A range estimation algorithm 315 estimates the range for the processed pixels from algorithm 310. This range estimation may be continuous or the pixels may be estimated with regard to range bins. For example, the field of view imaged by sensor 105 may be divided into four range bins of equal range extent. All pixels within a given bin are considered to have the same range to reduce computation complexity. The pre-processing of the frame sequences finishes through a feature extraction algorithm 320. Algorithm 320 extracts the features (except for the range feature, which as discussed above is extracted by algorithm 315) used by LBM 110 and OM 120 to characterize the likelihood of the pixel models. If both LBM 110 and OM 120 are sufficiently unlikely, the pixel is deemed to be representing oil. Example features include pixel intensity, local contrast (texture), or other suitable image characteristics.

With the features extracted and the pre-processing completed, LBM 110 evaluated and updated accordingly. In that regard, there may or may not be an initial period in which LBM 110 is initially created. For example, if there is no such initial period then LBM 110 is created on the fly as it is updated. Such an on-the-fly creation of LBM 110 will necessarily involve a relatively large frequency of false alarms until LBM 110 stabilizes. Alternatively, an offline initial period (not illustrated) may be used to process some initial image frames to create LBM 110. As each frames is pre-processed and feature-extracted, the resulting features may be used to evaluate the likelihood of the pixels' LBMs in a step 325. The local background model for each pixel may then be updated responsive to the current pixels in a step 330. This updating is damped to prevent a short sequence of anomalous events from skewing the local background model.

Figure 4:
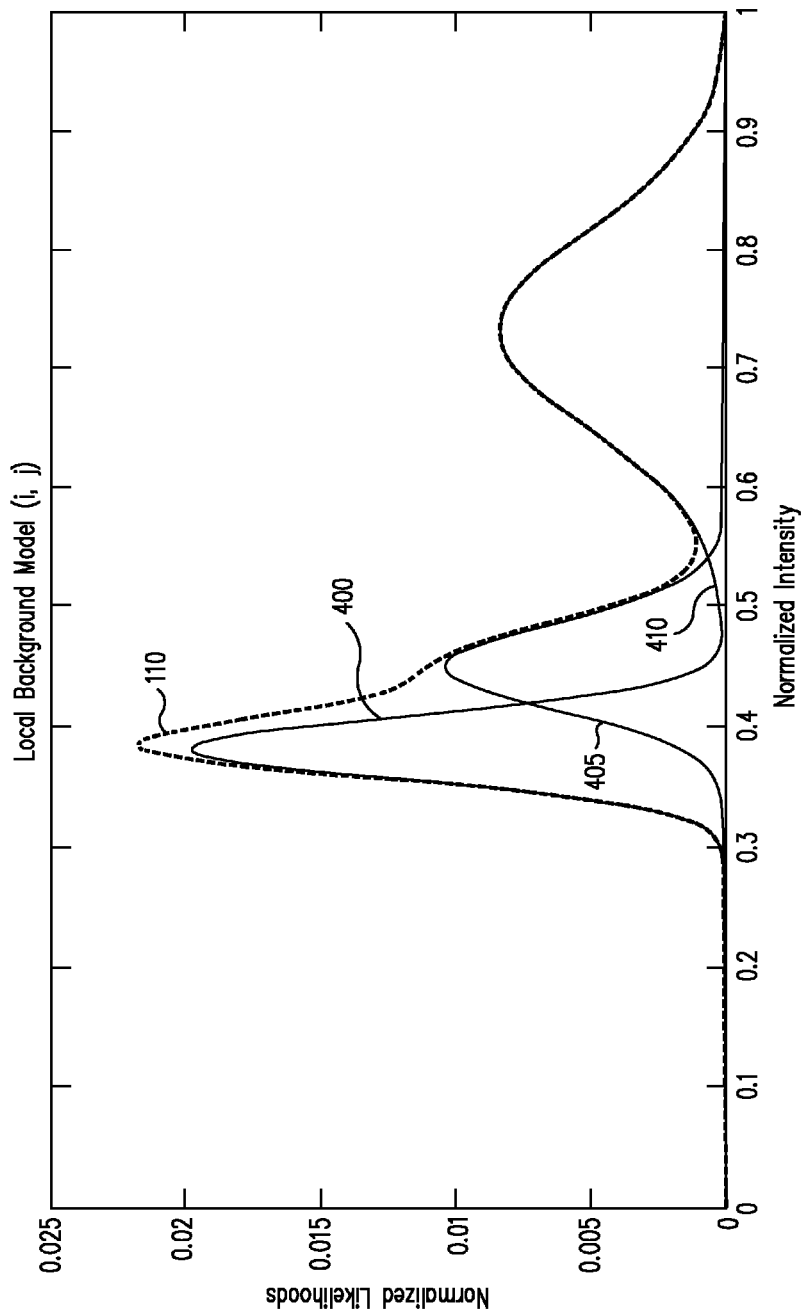
FIG. 4 illustrates an example local background model's likelihood function.

Although LBM 110 may be implemented using multiple features, the following example embodiment for LBM 110 uses just the pixel intensity as the sole extracted feature having a statistical behavior modeled by the local background model. This statistical behavior may be modeled using any of a variety of statistical models such as a mixture of Gaussians model (MGM). Alternatively, a histogram approach may be used to model the statistical behavior. For an MGM embodiment, the number of Gaussians used to model the observed pixel intensity is a design choice that depends upon the desired accuracy vs. the resulting computation complexity. The following example assumes that three Gaussians are used to model the pixel intensity under LBM 110. FIG. 4 shows these 3 Gaussians as curves 400, 405, and 410. These 3 Gaussians are weighted and summed to produce an LBM model 110 for a given pixel in the ith row and the jth column in the image frame. It may be seen that since three Gaussians are used to build LBM 110, LBM 110 is completely described by nine factors: the mean and standard deviation for each Gaussian as well as each Gaussian's weight factor. Given such an LBM 110, it may be readily observed that if an observed normalized intensity for that pixel is in the range of 0.0 to approximately 0.29, then the normalized likelihood that LBM 110 describes such behavior is essentially zero. Such a normalized intensity value is thus representing a statistically anomalous event for that pixel with regard to its local background behavior as modeled under LBM 110. However, such an observation, although locally quite unlikely, may turn out to be statistically non-anomalous as determined under OM 120. Examples of such frequently-observed anomalies that we do not wish to detect include glint off wave crests, dark intensities in wave shadows, stationary clutter objects, and moving clutter objects such as kelp.

Referring back to FIG. 3, a relatively rare observation as calculated by LBM 110 may thus be considered statistically likely as being an already-characterized outlier by OM 120. In that regard, each pixel is evaluated under OM 120 in a step 335 to determine whether its OM-evaluated features as extracted in step 320 indicate that those observed extracted features represent a statistically likely event for that pixel under OM 120. Just like LBM 110, OM 120 may be represented using any suitable statistical model such as a mixture of Gaussians model (MGM). Alternatively, OM 120 may be modeled using histograms. In the following example, OM 120 will be assumed to be represented by twenty-Gaussian-containing MGM. However, the extracted features for OM 120 are multi-dimensional. For example, the extracted features for a pixel (i,j) may be represented by a vector $x_{i,j}$. The dimensionality of this vector depends upon a particular designs tradeoff between accuracy and computation complexity. In one embodiment, the extracted feature vector was three-dimensional such that three features were extracted for each pixel to evaluate it under OM 120. For example, the three extracted features may comprise range, intensity, and contrast. Because of this multi-dimensionality, OM 120 can be completely characterized by the Gaussian means and the covariances as well as the weight given to each Gaussian. If OM 120 is modeled using an MGM, it may be represented as:

$$P_{OM}(x) = \sum_k \gamma_k p_k(x | \Theta_k),$$

where $$p_k(x | \Theta_k) \sim N\left(\Theta_k = \left\{\mu_k, \sum_k\right\}\right),$$

where $p_{OM}(x)$ is the likelihood of OM 120 evaluated for feature vector x, k indexes the components in the MGM, $\gamma_k$ is the weight of the k-th component, $p_k(x|\Theta_k)$ is the likelihood of component k$\Theta_k$ is the set of parameters for feature vector x, and N( ) indicates a Gaussian distribution.

Figure 5A:
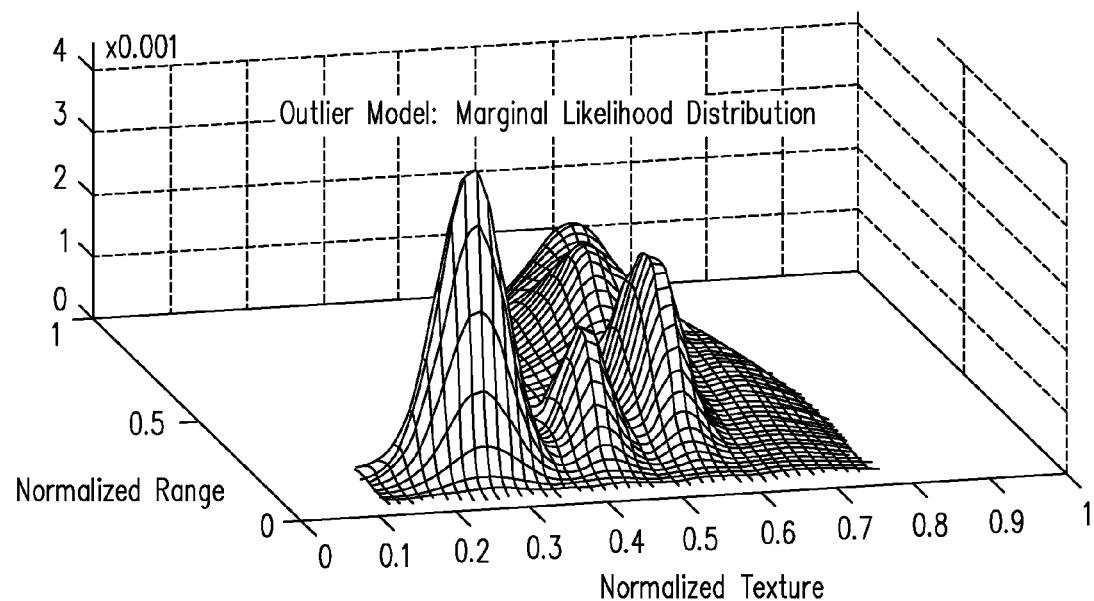
FIG. 5a illustrates an example outlier model's marginal likelihood function based upon normalized range and texture.
Figure 5B:
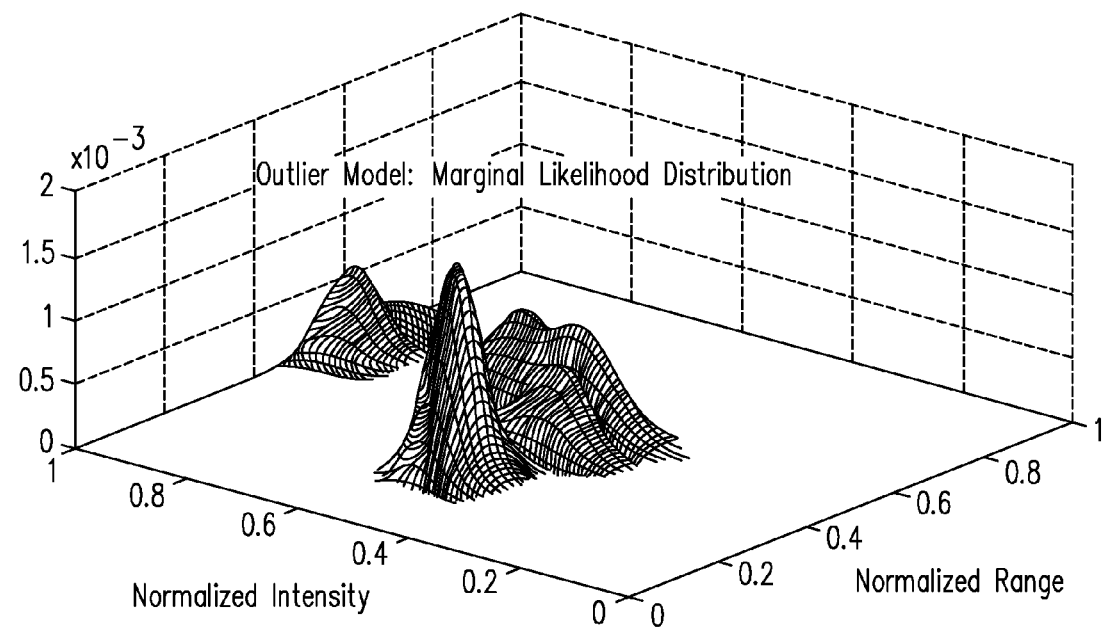
FIG. 5b illustrates an example outlier model's marginal likelihood function based upon normalized range and intensity.

The resulting OM 120 is The resulting OM 120 thus contains three independent variables, and a likelihood may be evaluated for each possible combination of these three variables. In that regard, OM 120 is illustrated using marginal likelihoods as seen in FIGS. 5a and 5b. FIG. 5a shows the marginal likelihood for OM 120 based solely upon normalized range and normalized texture whereas FIG. 5b shows the marginal likelihood for OM 120 based solely upon normalized intensity and normalized range.

As discussed above, OM 120 is updated more heavily by statistically unlikely observations as opposed to a feature observation that is deemed to be more common. In that regard, OM 120 can be updated by weighting each pixel. Alternatively, just a fraction of the total pixels in any given frame may be identified as being worthy of weights—for example, the pixels having the top 40% least likely scores from their LBMs may be used to update OM 120. Regardless of whether all pixels are used in this fashion or just a fraction of the pixels are used, the resulting pixels may be weighted according to their probability under their LBM and also normalized to compensate for the non-uniform distribution of feature values as represented by a step 340. For example the weight given to pixel (i,j) may be represented by $w(x_{i,j})$ as evaluated by the following expression:

$$w(x_{i,j}) = \frac{1}{p_{LBM(i,j)}(x_{i,j}) \cdot n(x_{i,j})},$$

where, for example, $$n(x_{i,j}) = \prod_l p_{CF(l)}^{ne}(x_{i,j}(l)),$$

where $x_{i,j}$ is the feature vector extracted for pixel (i,j), $p_{LBM(i,j)}(x_{i,j})$ is the likelihood of LBM(i,j) given $x_{i,j}$, is the normalization applied for the feature observation $x_{i,j}$, 1 is the dimensionality of $x_{i,j}$, $p_{CF(l)}($ ) is the marginal likelihood distribution (computed using empirical statistics in the current frame) in dimension 1, and ne is an exponent, e.g., 1/l. OM 120 may then be updated in a step 345 based upon the resulting weighted and normalized pixels. The end result is that pixels generating small likelihoods under LBM 110 will be assigned large weights in updating OM 120.

With OM 120 thus evaluated and updated, detection algorithm 125 may now be executed. To do so, a scene anomaly likelihood calculation step 350 may be implemented for each pixel that calculates the product of the likelihood for its LBM 110 and OM 120. Such a single frame likelihood may be temporally integrated over several frames in a step 355 to produce a time averaged local likelihood (TALL). Moreover, the TALL values from step 355 may be spatially averaged in a step 360 to remove spurious (because of their pixel isolation) low likelihood samples. The resulting TALL distribution for all the pixels may have its statistical properties characterized such as by a mean (denoted as MEAN_TALL) and a standard deviation (denoted as STD_TALL) in a detection step 365. Should some region in the TALL distribution across the pixels be statistically anomalous such as by having a time averaged local likelihood of less than MEAN_TALL minus S*STD_TALL, where S is an empirically defined number, than that region may be flagged as containing oil.

Note the power of the LBM/OM combination in that a human observer may then determine that the oil detection from step 365 was actually a false alarm. In such a case, the pixel data may always be stored in a memory such as discussed above with regard to memory 220 so that OM 120 may be updated to include the extracted features that were identified as oil as instead being part of OM 120. In this fashion, algorithm 300 may continually be improved and "learn" the distinction between oil and other outlier events.

It will be appreciated that while LBM 110 and OM 120 have been described with regard to a fixed field of view, the algorithm may readily be extended to include a panning of sensor 105 across water surface 104. Sensor 105 could be panned to a first field of view having its own LBMs and OM, then to a second field of view having its own LBMs and OM, and so on. In this fashion, a relatively vast water surface could be scanned by sensor 105. Moreover, LBM 110 and OM 120 are readily extended to a moving platform in this fashion as well.

Figure 6:
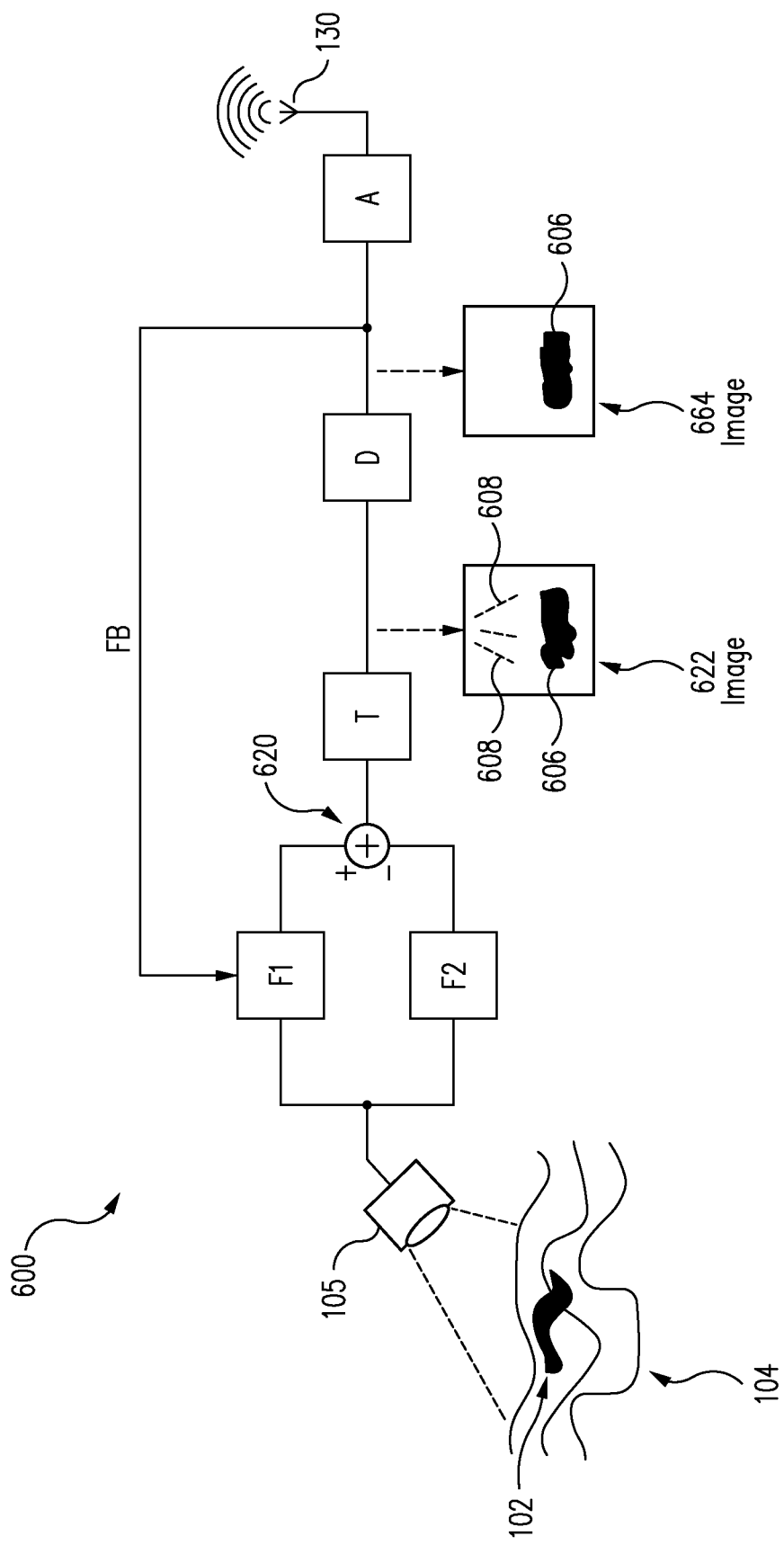
FIG. 6 shows an overview of a simplified oil detection process in which excludes an outlier model evaluation and updating.

Other alternatives include simplifying the signal processing by only performing a local analysis without performing any sort of outlier analysis. Although such an abbreviated analysis runs the risk of falsely identifying outliers such as glint, kelp, etc. as oil, the false alarm rate may be acceptable in some circumstances. An example of such an oil detection algorithm is shown in FIG. 6 for an infrared imaging system 600. In one embodiment, a first temporal IIR filter (F1) is applied to the captured image from sensor 105 to provide a strongly damped IIR filtering scheme. In one aspect, the image from the first temporal IIR filter (F1) is very slowly changing and will change only with changing conditions during the day, such as the sun moving and wave state changing. It may thus be appreciated that an output of F1 represents a local background model for a given pixel.

In one embodiment, a second temporal IIR filter (F2) is applied to the captured image to provide a moderately damped IIR filtering scheme. In one aspect, the image from the second temporal IIR filter (F2) is slowly changing and may not pick up sudden changes, such as the sun or sky reflecting on the surface or waves breaking. However, slower events, such as oil forming on the water, may cause this image to change.

In accordance with one or more embodiments, the first IIR filter (F1) and the second IIR filter (F2) may be represented by the equations set forth below:

$$S_{F1}^t = D^1 \times S_{F1}^{t-1} + (1-D^1) \times S^t$$

$$S_{F2}^t = D^2 \times S_{F2}^{t-1} + (1-D^2) \times S^t$$

$$0 < D^2 < D^1 < 1$$

where $S_{F1}^t$ is the signal (S) after the first filter (F1) at time t; $S_{F2}^t$ is the signal (S) after the second filter (F2) at time t; $S_{F1}^{t-1}$ is the signal (S) after the first filter (F1) at time t−1 (e.g., the previous video frame); $S_{F2}^{t-1}$ is the signal (S) after the second filter (F2) at time t−1 (e.g., the previous video frame); $D^1$ is the damping factor for the first filter (F1); and $D^2$ is the damping factor for the second filter (F2).

In one embodiment, a difference image (F1−F2) is created (620) by subtracting the resulting image from the first IIR filter (F1) from the resulting image from the second IIR filter (F2). The images may represent snapshots, video, etc., without departing from the scope of the present disclosure.

In one embodiment, pixel positions where the difference is greater (i.e., positive or negative difference) than a threshold (T) are determined to be a potential petroleum spill, as shown by image 622. For example, in image 622, a large petroleum cluster is labeled as cluster 606 (e.g., representing an image of petroleum spill 102 on water 104), while smaller single pixel occurrences that exceed the threshold (T) are labeled as elements 608. In an embodiment, these single or a few grouped pixel occurrences 608 or clusters comprising small isolated potential petroleum spill detections are marked as and considered false alarms and may be removed from the infrared image data or considered as not valid detections. In one embodiment, once the process of determining valid detections (D) is complete (i.e., occurrences that exceed the threshold (T) and that are considered valid detections (D)), the remaining valid detections (D) may be viewed, for example, as shown in image 624. As an example for an embodiment, cluster 606 in image 624 may be colorized or otherwise marked, as would be understood by one skilled in the art, for quick identification by a user.

In one embodiment, areas of the infrared image where the petroleum spill is detected (e.g., cluster 606) may be fed back (FB) (e.g., to the first temporal IIR filter (F1)) such that the valid petroleum spill detections remain in the resulting difference image and are not filtered out, as would be understood by one skilled in the art. In this fashion, the local background model developed by F1 is not updated on oil. For example for one or more embodiments, updating of the strongly damped signal $S_{F1}^t$ is turned off for areas labeled as a potential petroleum spill (e.g., valid detections) by setting $D_{i,j}^1 = 1$ for all pixels at coordinates (i,j) associated with the potential petroleum spill.

In one embodiment, if a petroleum spill persists and is considered a valid detection (e.g., as shown in image 624) for some predefined number of frames, an alarm (A) may be provided as an alert (e.g., an automated detection and alert algorithm). For example, the alarm may be audible and/or provided via email or other notification means to a user defined phone number, address, and/or some other conventional alert method. In one aspect, the alarm (A) may include an audible alarm via a loudspeaker, public address (PA) system, etc. In another aspect, the alarm (A) may include a wireless transmission via an antenna 130 to a remote device, such as a radio, walkie talkie, mobile phone, etc. It should be appreciated that one or more alarm notifications may be sent to one or more users, operators, administrators, etc, by various means, without departing from the scope of the present disclosure.

Where applicable, various embodiments of the invention may be implemented using hardware, software, or various combinations of hardware and software. Where applicable, various hardware components and/or software components set forth herein may be combined into composite components comprising software, hardware, and/or both without departing from the scope and functionality of the present disclosure. Where applicable, various hardware components and/or software components set forth herein may be separated into subcomponents having software, hardware, and/or both without departing from the scope and functionality of the present disclosure. Where applicable, it is contemplated that software components may be implemented as hardware components and vice-versa.

Software, in accordance with the present disclosure, such as program code and/or data, may be stored on one or more computer readable mediums. It is also contemplated that software identified herein may be implemented using one or more general purpose or specific purpose computers and/or computer systems, networked and/or otherwise. Where applicable, ordering of various steps described herein may be changed, combined into composite steps, and/or separated into sub-steps to provide features described herein.

In various embodiments, software for detection module 112 and mode modules 114A-114N may be embedded (i.e., hard-coded) in processing component 110 or stored on memory component 120 for access and execution by processing component 110. In one aspect, code (e.g., software and/or embedded hardware) for detection module 112 and mode modules 114A-114N may be adapted to define preset display functions that allow processing component 110 to automatically switch between various processing techniques for sensed modes of operation, as described herein.

Embodiments described above illustrate but do not limit the disclosure. It should also be understood that numerous modifications and variations are possible in accordance with the principles of the present disclosure. Accordingly, the scope of the disclosure is defined only by the following claims.

What is claimed is:

1. An infrared camera system, comprising:
a sensor adapted to capture a current image of a body of water and a plurality of preceding images of the body of water, wherein the current image and each preceding image all comprise a plurality of digital pixels; and
a processor adapted to:
determine a plurality of local background models for the plurality of digital pixels in the plurality of preceding images such that each digital pixel corresponds on a one-to-one basis with the corresponding local background model;
evaluate each digital pixel in the current image with the corresponding local background model; and
detect a petroleum-containing contaminant on the body of water responsive to at least the local background model evaluation for each digital pixel.

2. The infrared camera system of claim 1, wherein the processor is further adapted to:
evaluate a second set of features from the each digital pixel with regard to an outlier model; and
detect the petroleum-containing contaminant further responsive to at least the outlier model evaluation.

3. The infrared camera system of claim 2, wherein the outlier model comprises a single outlier model.

4. The infrared camera system of claim 2, wherein the first set of features comprises an intensity for each pixel, and wherein the evaluation with regard to the local background model comprises determining a likelihood of the pixel intensity in light of the local background model.

5. The infrared camera system of claim 4, wherein the processor is further adapted to determine a likelihood of the extracted features in light of the outlier model.

6. The infrared camera system of claim 5, wherein the processor is further adapted to identify pixels whose extracted features are relatively unlikely under both the outlier model and the local background model, wherein the identified pixels correspond to the detected petroleum-containing contaminant.

7. The infrared camera system of claim 1, wherein the plurality of digital pixels is downsampled pixels.

8. A method of detecting a petroleum-containing contaminant within an infrared image comprised of a plurality of digital pixels, the method comprising:
developing a plurality of local background models for a plurality of digital pixels in a plurality of proceeding images, wherein each digital pixel corresponds on a one-to-one basis with the corresponding local background model and the local background model models statistical behavior for at least one feature of the pixel;
extracting the at least one feature from each of the pixels;
determining a likelihood for the extracted feature in light of each corresponding local background model; and
detecting contaminant-containing pixels within the infrared image responsive to at least the determined likelihoods for each digital pixel.

9. The method of claim 8, wherein the at least one extracted feature comprises a pixel intensity.

10. The method of claim 9, wherein the at least one extracted feature further comprises a pixel contrast.

11. The method of claim 10, wherein the at least one extracted feature further comprises a pixel texture.

12. The method of claim 8, further comprising:
developing an outlier model, wherein the outlier model models the statistical behavior for the at least one extracted feature for pixels identified as corresponding to relatively unlikely to occur in light of the local background models; and
determining a likelihood for the feature in light of the outlier model for each of the pixels, wherein the detection of the contaminant-containing pixels is further responsive to outlier model likelihoods.

13. The model of claim 12, wherein the statistical behavior modeled by each of the local background models and by the outlier model is in the absence of contaminant.

14. The model of claim 12, further comprising updating each of the local background models responsive to the extracted features.

15. The model of claim 14, further comprising weighting each pixel according to the likelihood of the extracted feature in light of the corresponding local background model.

16. The model of claim 15, further comprising updating the outlier model responsive to pixel weights.

17. The method of claim 8, wherein the plurality of digital pixels is downsampled pixels.

18. A method, comprising
sensing a first infrared image frame of an ocean surface; wherein the infrared image frame comprises a plurality of digital pixels;
for each pixel, modeling a statistical behavior of at least one extracted image feature using a mixture of Gaussians model (MGM), each pixel thereby corresponding to a local background model that corresponds to the modeled statistical behavior;
sensing a second infrared image frame of the ocean surface;
for each pixel in the second infrared image frame, extracting the at least one image feature;
for each pixel in the second infrared image frame, determining a likelihood of the at least one image feature in light of corresponding local background model, wherein each pixel in the second infrared image frame corresponds on a one-to-one basis with the corresponding local background model; and
detecting any oil-containing pixels in the second infrared image responsive to the determined likelihoods.

19. The method of claim 18, wherein the MGM comprise three Gaussians.

20. The method of claim 18, further comprising updating each local background model if no oil-containing pixels are detected.

* * * * *